United States Patent
Lee et al.

(10) Patent No.: US 11,540,727 B2
(45) Date of Patent: Jan. 3, 2023

(54) APPARATUS AND METHOD FOR MEASURING BIO-SIGNAL

(71) Applicant: SAMSUNG ELECTRONICS CO., LTD., Suwon-si (KR)

(72) Inventors: Jong Wook Lee, Suwon-si (KR); Byung Hoon Ko, Hwaseong-si (KR); Chang Mok Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 199 days.

(21) Appl. No.: 16/566,218

(22) Filed: Sep. 10, 2019

(65) Prior Publication Data
US 2020/0077901 A1 Mar. 12, 2020

(30) Foreign Application Priority Data
Sep. 11, 2018 (KR) .......... 10-2018-0108499

(51) Int. Cl.
*A61B 5/0205* (2006.01)
*A61B 5/02* (2006.01)
(Continued)

(52) U.S. Cl.
CPC ........ *A61B 5/0205* (2013.01); *A61B 5/02007* (2013.01); *A61B 5/165* (2013.01);
(Continued)

(58) Field of Classification Search
CPC ... A61B 5/0205; A61B 5/02007; A61B 5/681; A61B 5/02108; A61B 5/02416;
(Continued)

(56) References Cited

U.S. PATENT DOCUMENTS 5,976,088 A * 11/1999 Urbano ............... G01S 7/52066
600/443
9,610,018 B2 4/2017 Gulati et al.
(Continued)

FOREIGN PATENT DOCUMENTS

JP WO2016/024495 A1 2/2016
KR 10-2017-0127744 A 11/2017

OTHER PUBLICATIONS

Lai & Kim, "Lightweight wrist photoplethysmography for heavy exercise: motion robust heart rate monitoring algorithm", Feb. 2015, Healthcare Technology Letters, vol. 2, Iss. 1, p. 6-11, 6 pages total.
(Continued)

*Primary Examiner* — Lynsey C Eiseman
*Assistant Examiner* — Jessica L Mullins
(74) *Attorney, Agent, or Firm* — Sughrue Mion, PLLC

(57) ABSTRACT

An apparatus for measuring a bio-signal includes a pulse wave sensor that may measure a pulse wave signal, of an object of interest, that is non-equidistantly sampled based on a sampling rate of the pulse wave sensor, and a processor that may identify, using a sampling profile, a first interval based on a health index to be measured. The processor may identify, using the sampling profile, a second interval based on the health index to be measured. The processor may set the sampling rate of the pulse wave sensor to a first sampling rate in the first interval. The processor may set the sampling rate of the pulse wave sensor to a second sampling rate, that is less than the first sampling rate, in the second interval.

19 Claims, 10 Drawing Sheets

(51) Int. Cl.
*A61B 5/00* (2006.01)
*A61B 5/16* (2006.01)
*A61B 5/024* (2006.01)
*A61B 5/021* (2006.01)

(52) U.S. Cl.
CPC .......... *A61B 5/681* (2013.01); *A61B 5/02108* (2013.01); *A61B 5/02416* (2013.01)

(58) Field of Classification Search
CPC . A61B 5/14522; A61B 5/0059; A61B 5/7203; A61B 6/5205; A61B 8/5207; G61B 8/5207
See application file for complete search history.

(56) References Cited

U.S. PATENT DOCUMENTS

| | | |
|---|---|---|
| 9,707,466 B2 | 7/2017 | Bleich et al. |
| 9,717,424 B2 | 8/2017 | Kulach |
| 9,968,270 B1 | 5/2018 | Murphy et al. |
| 10,103,765 B2 | 10/2018 | Shim et al. |
| 2003/0212336 A1* | 11/2003 | Lee .................. A61B 5/726 600/504 |
| 2015/0335288 A1* | 11/2015 | Toth .................. A61B 5/6833 600/373 |
| 2017/0014037 A1 | 1/2017 | Coppola et al. |
| 2017/0095211 A1 | 4/2017 | Wang et al. |
| 2017/0128020 A1 | 5/2017 | Olivier et al. |
| 2017/0209055 A1* | 7/2017 | Pantelopoulos ..... A61B 5/7203 |
| 2017/0224244 A1 | 8/2017 | Kuwabara et al. |
| 2017/0331505 A1 | 11/2017 | Shim et al. |
| 2018/0000424 A1 | 1/2018 | Demirtas et al. |
| 2018/0028077 A1 | 2/2018 | Wu et al. |
| 2018/0184975 A1* | 7/2018 | Kaasinen ............. A61B 5/0002 |

OTHER PUBLICATIONS

Choi and Shin, "Photoplethysmography sampling frequency: pilot assessment of how low can we go to analyze pulse rate variability with reliability?", 2017, Physiological Measurement, p. 586-600, 16 pages total.

* cited by examiner

APPARATUS AND METHOD FOR MEASURING BIO-SIGNAL

CROSS-REFERENCE TO RELATED APPLICATION(S)

This application claims priority under 35 U.S.C. § 119 to Korean Patent Application No. 10-2018-0108499, filed on Sep. 11, 2018, in the Korean Intellectual Property Office, the disclosure of which is incorporated by reference herein in its entirety.

BACKGROUND

1. Field

The present disclosure relates to a technology for measuring a bio-signal.

2. Description of Related Art

Healthcare technology has attracted much attention due to the rapid entry into an aging society and relevant social problems such as an increase in medical expenses. Accordingly, medical devices that can be utilized by hospitals and inspection agencies, and also small-sized medical devices that can be carried by individuals, such as wearable devices, are being developed.

A small-sized medical device is worn by a user in the form of a wearable device configured to directly measure a user's heart rate, stress index, or the like, so that the user can directly measure and manage heart rate, stress index, etc.

Therefore, research regarding miniaturization of devices for measuring a health index, such as heart rate, stress index, or the like, has been actively conducted. However, a small-sized device operates with a small battery, and hence there is a need for a technology for accurately measuring a health index while reducing power consumption.

SUMMARY

Example embodiments relate to an apparatus and method for measuring a bio-signal, which adjust a sampling rate of a pulse wave sensor according to a health index.

In accordance with an aspect of an example embodiment, there is provided an apparatus for measuring a bio-signal including a pulse wave sensor that may measure a pulse wave signal, of an object of interest, that is non-equidistantly sampled based on a sampling rate of the pulse wave sensor, and a processor that may identify, using a sampling profile, a first interval based on a health index to be measured. The processor may identify, using the sampling profile, a second interval based on the health index to be measured. The processor may set the sampling rate of the pulse wave sensor to a first sampling rate in the first interval. The processor may set the sampling rate of the pulse wave sensor to a second sampling rate, that is less than the first sampling rate, in the second interval.

The pulse wave signal may be a photoplethysmogram (PPG) signal.

The health index may include at least one of heart rate, blood vessel stiffness, stress index, and blood pressure.

The sampling profile may store information that maps the health index to be measured, the first interval, and the second interval.

The processor may identify a predetermined interval including an onset point of a heartbeat as the first interval, and identify a remaining interval as the second interval based on the health index to be measured being at least one of heart rate, blood vessel stiffness, or stress index.

The processor may identify a systolic period of a heartbeat as the first interval, and identify a remaining interval as the second interval based on the health index to be measured being blood pressure.

The processor may generate an equidistantly sampled pulse wave signal by resampling the non-equidistantly sampled pulse wave signal.

The processor may identify at least one of an onset point of a heartbeat, a systolic period of a heartbeat, and a heartbeat cycle by analyzing the generated equidistantly sampled pulse wave signal, and update the sampling profile based on the onset point of the heartbeat, the systolic period of the heartbeat, or the heartbeat cycle.

The processor may identify the health index by analyzing the equidistantly sampled pulse wave signal.

The processor may identify that the equidistantly sampled pulse wave signal is an abnormal heartbeat signal, and deactivate a sampling rate control function based on identifying that the equidistantly sampled pulse wave signal is the abnormal heartbeat signal.

In accordance with an aspect of an example embodiment, there is provided a method of measuring a bio-signal including identifying, using a sampling profile, a first interval and a second interval based on a health index to be measured. The method may include setting a sampling rate of a pulse wave sensor to a first sampling rate in the first interval. The method may include setting the sampling rate of the pulse wave sensor to a second sampling rate, that is less than the first sampling rate, in the second interval. The method may include measuring a pulse wave signal of an object of interest that is non-equidistantly sampled based the sampling rate of the pulse wave sensor.

The pulse wave signal may be a photoplethysmogram (PPG) signal.

The health index may include at least one of heart rate, blood vessel stiffness, stress index, and blood pressure.

The sampling profile may store information that maps the health index, the first interval, and the second interval.

The identifying of the first interval and the second interval may include identifying a predetermined interval including an onset point of a heartbeat as the first interval and identifying a remaining interval as the second interval based on the health index to be measured being heart rate, blood vessel stiffness, or stress index.

The identifying of the first interval and the second interval may include identifying a systolic period of a heartbeat as the first interval and identifying a remaining interval as the second interval based on the health index to be measured being blood pressure.

The method may further include generating an equidistantly sampled pulse wave signal by resampling the non-equidistantly sampled pulse wave signal.

The method may further include identifying at least one of an onset point of a heartbeat, a systolic period of a heartbeat, and a heartbeat cycle by analyzing the generated equidistantly sampled pulse wave signal, and updating the sampling profile based on the onset point of the heartbeat, the systolic period of the heartbeat, or the heartbeat cycle.

The method may further include identifying the health index by analyzing the equidistantly sampled pulse wave signal.

The method may further include identifying that the equidistantly sampled pulse wave signal is an abnormal heartbeat signal, and deactivating a sampling rate control function based on identifying that the equidistantly sampled pulse wave signal is the abnormal heartbeat signal.

Other features and aspects will be apparent from the following detailed description, the drawings, and the claims.

BRIEF DESCRIPTION OF THE DRAWINGS

The above and/or other aspects, features, and advantages of certain embodiments of the present disclosure will be more apparent from the following description taken in conjunction with the accompanying drawings, in which.

DETAILED DESCRIPTION

Figure 1:
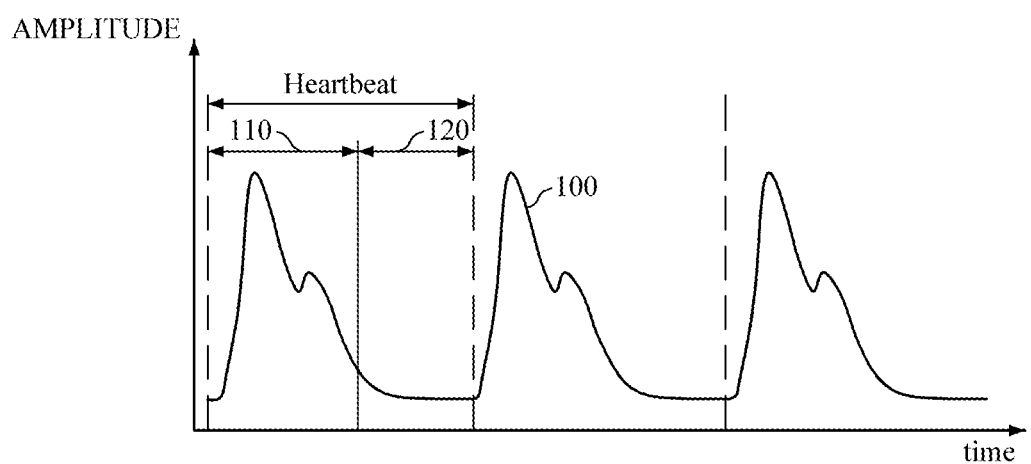
FIG. 1 is a graph illustrating a pulse wave signal according to an example embodiment.

Example embodiments are described in greater detail below with reference to the accompanying drawings. In the following description, like drawing reference numerals are used for like elements. The matters described in the description, such as detailed construction and elements, are provided to assist in a comprehensive understanding of the example embodiments. However, it should be apparent that the example embodiments can be practiced without those specifically described matters. Also, well-known functions or constructions might not be described in detail since they might obscure the description with unnecessary detail.

Throughout the drawings and the detailed description, unless otherwise described, the same drawing reference numerals should be understood to refer to the same elements, features, and structures. The relative size and depiction of these elements may be exaggerated for clarity, illustration, and convenience.

It should be noted that in some alternative implementations, the functions/acts noted in the blocks may occur in a different order than as noted in the flowcharts. For example, two blocks shown in succession may in fact be executed substantially concurrently or the blocks may be executed in the reverse order, depending upon the functionality/acts involved.

Terms described below are selected by considering functions in the example embodiments and meanings may vary depending on, for example, a user or operator's intentions or customs. Therefore, in the following example embodiments, when terms are specifically defined, the meanings of the terms should be interpreted based on definitions, and otherwise, should be interpreted based on general meanings recognized by those skilled in the art.

It should be understood that, although the terms "first," "second," etc., may be used herein to describe various elements, these elements should not be limited by these terms. These terms are used to distinguish one element from another. Also, the singular forms of terms are intended to include the plural forms of the terms as well, unless the context clearly indicates otherwise. In the specification, unless explicitly described to the contrary, the word "comprise," and variations such as "comprises" or "comprising," should be understood to imply the inclusion of stated elements but not the exclusion of any other elements. Terms such as "unit" and "module" denote units that process at least one function or operation, and that may be implemented by hardware, software, or a combination of hardware and software.

As used herein, expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

It should also be understood that the elements or components in the following description are discriminated in accordance with their respective main functions. In other words, two or more elements may be integrated into a single element or a single element may be divided into two or more elements in accordance with a subdivided function. Additionally, each of the elements in the following description may perform a part or whole of the function of another element as well as its main function, and some of the main functions of each of the elements may be performed exclusively by other elements. Each element may be realized in the form of a hardware component, a software component, and/or a combination thereof.

FIG. 1 is a graph illustrating a pulse wave signal according to an example embodiment. Specifically, FIG. 1 illustrates a photoplethysmogram (PPG) signal corresponding to three consecutive heartbeats.

Referring to FIG. 1, a waveform of the pulse wave signal 100 is a summation of a propagation wave propagating from the heart to peripheral parts of the body and reflection waves returning from the peripheral parts of the body. Further, a cycle of the pulse wave signal may coincide with a heartbeat cycle. The pulse wave signal of one cycle may be classified into a systolic portion 110 and a diastolic portion 120 of a heartbeat.

Figure 2:
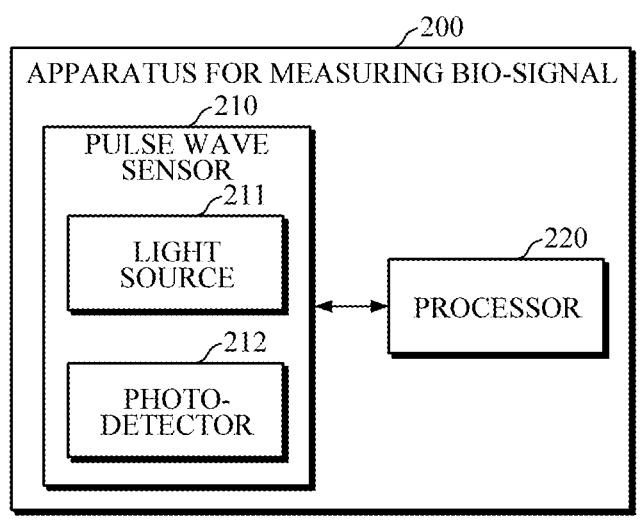
FIG. 2 is a block diagram illustrating an apparatus for measuring a bio-signal according to an example embodiment.

FIG. 2 is a block diagram illustrating an apparatus for measuring a bio-signal according to an example embodiment. The apparatus 200 for measuring a bio-signal as shown in FIG. 2 is an apparatus configured to measure a pulse wave signal by adjusting a sampling rate of a pulse wave sensor 210 based on a health index to be measured, and may be disposed in an electronic device. In this case, the electronic device may be a mobile phone, a smartphone, a tablet computer, a notebook computer, a personal digital assistant (PDA), a portable multimedia player (PMP), a navigation system, an MP3 player, a digital camera, a wearable device, and the like. The wearable device may include a wearable device of various types, such as a wrist watch type, a wrist band type, a ring type, a belt type, a necklace type, an ankle band type, a thigh band type, a forearm band type, and the like. However, the electronic device and the wearable devices are not limited to the aforementioned examples.

Referring to FIG. 2, the apparatus 200 for measuring a bio-signal may include the pulse wave sensor 210 and a processor 220.

The pulse wave sensor 210 may measure a pulse wave signal of an object of interest. The object of interest, which is an object for measuring a pulse wave signal, may be a body, a body region, a body part, or the like, and may be in contact with the pulse wave sensor 210. For example, the object of interest may be a human body part adjacent to a radial artery on a surface of a wrist. As another example, the object of interest may be a human body peripheral part, such as a finger, a toe, an earlobe, or the like. The pulse wave signal may be a PPG signal. According to an example embodiment, when the object of interest is in contact with the pulse wave sensor 210, the pulse wave sensor 210 may emit light of a predetermined wavelength towards the object of interest, and measure a pulse wave signal of the object of interest by receiving light reflected by the object.

The pulse wave sensor 210 may measure the pulse wave signal at a first sampling rate in a first interval based on a control signal of the processor 220, and measure the pulse wave signal at a second sampling rate in a second interval. The second sampling rate may be less than the first sampling rate.

As shown in FIG. 2, the pulse wave sensor 210 may include a light source 211, and a photodetector 212.

The light source 211 may emit light of a predetermined wavelength towards the object of interest that is in contact with the pulse wave sensor 210. For example, the light source 211 may emit visible light or infrared light towards the object of interest. However, the wavelength of light that is emitted by the light source 211 may vary based on the measurement purpose, a target component to be measured, the object of interest, or the like. In addition, the light source 211 may be configured with a single light source, or may be configured in the form of an array of multiple light sources. Further, each of the light sources may emit light rays having the same wavelength, or light rays having different wavelengths. The light source 211 may include a light emitting diode (LED), a laser diode, a phosphor, and the like.

The photodetector 212 may measure a pulse wave signal of the object of interest by receiving light reflected by the object irradiated by the light source 211. According to an example embodiment, the photodetector 212 may include a photodiode, a photo transistor, a charge-coupled device (CCD), and the like. The photodetector 212 may be configured with a single element, or may be configured in the form of an array of multiple elements.

The processor 220 may control an overall operation of the apparatus 200 for measuring a bio-signal.

When a sampling rate control function is activated, the processor 220 may adjust a sampling rate of the pulse wave sensor 210 for each interval based on the health index to be measured, and identify a health index based on a pulse wave signal that is non-equidistantly sampled and measured by the pulse wave sensor 210. For example, the processor 220 may identify the first interval and the second interval based on a health index to be measured. In addition, the processor 220 may control the pulse wave sensor 210 to measure a non-equidistantly sampled pulse wave signal by setting a sampling rate of the pulse wave sensor 210 to the first sampling rate in the first interval, and setting the sampling rate of the pulse wave sensor 210 to the second sampling rate in the second interval. In addition, the processor 220 may identify a health index based on the measured and non-equidistantly sampled pulse wave signal. The health index may include heart rate, blood vessel stiffness, stress index, blood pressure, and the like.

Hereinafter, the processor 220 will be described in more detail with reference to FIG. 3.

Figure 3:
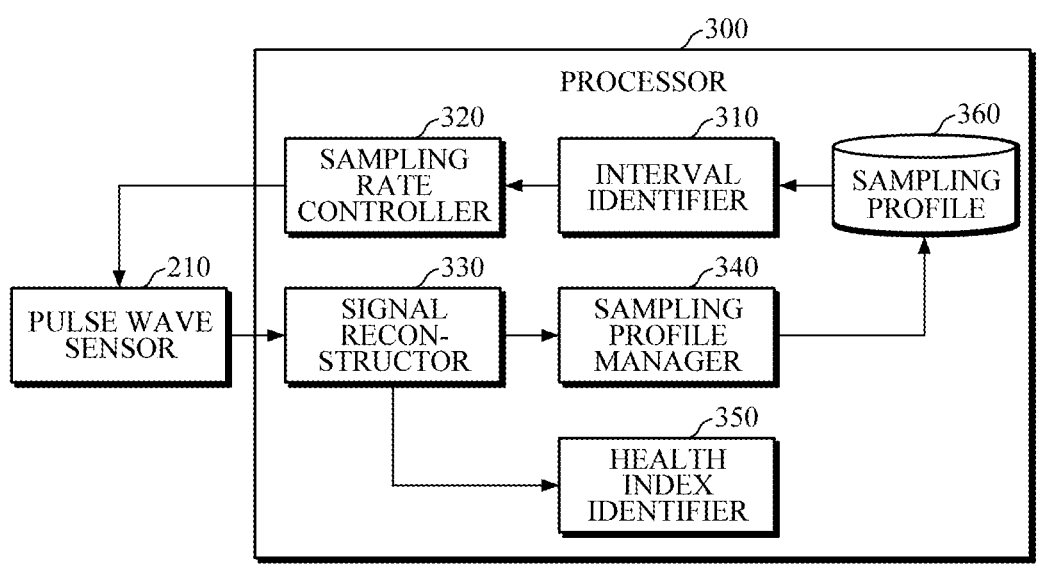
FIG. 3 is a block diagram illustrating a processor according to an example embodiment.

FIG. 3 is a block diagram illustrating a processor according to an example embodiment. The processor 300 shown in FIG. 3 may correspond to the processor 220 shown in FIG. 2.

Referring to FIG. 3, the processor 300 may include an interval identifier 310, a sampling rate controller 320, a signal reconstructor 330, a sampling profile manager 340, and a health index identifier 350.

The interval identifier 310 may identify a first interval to which a first sampling rate is applied, and a second interval to which a second sampling rate is applied. Further, the interval identifier 310 may identify the first interval and the second interval based a health index to be measured. Further still, the interval identifier 310 may identify the first interval and the second interval based a sampling profile 360. As described above, the health index may include heart rate, blood vessel stiffness, stress index, blood pressure, and the like, and the second sampling rate may be less than the first sampling rate.

The sampling profile 360 may store information that maps a health index and first and second intervals corresponding to the health index, and may be generated in advance by analyzing a pulse wave signal of the object of interest. The relative importance of each portion of the pulse wave signal may differ according to the health index. For example, in the case of estimating heart rate, pulse arrival time (PAT)-based blood vessel stiffness, or heart rate variability-based stress index, it might be more important to accurately measure a time of an onset point of a heartbeat, and therefore data within a predetermined interval including the onset point of the heartbeat might be more important than data in the remaining interval. As another example, in the case of blood pressure estimation using pulse waveform analysis (PWA), data is acquired from a systolic period of a heartbeat, and therefore data in the systolic period of the heartbeat might be more important than data in the remaining period. According to an example embodiment, when the health index is heart rate, stress index, or blood vessel stiffness, the sampling profile 360 may store information that identifies a predetermined interval including the onset point of the heartbeat as the first interval, and define the remaining interval other than the first interval as the second interval. In addition, when the health index is blood pressure, the sampling profile 360 may store information that identifies a systolic period of the heartbeat as the first interval, and identifies the remaining interval, i.e., a diastolic period of the heartbeat, other than the first interval as the second interval.

The sampling rate controller 320 may set a sampling rate of the pulse wave sensor 210 to the first sampling rate in the first interval, and set the sampling rate of the pulse wave sensor 210 to the second sampling rate in the second interval. The pulse wave sensor 210 may measure a pulse wave signal (hereinafter referred to as a "non-equidistant pulse wave signal") which is non-equidistantly sampled according to the sampling rate set by the sampling rate controller 320. In other words, the samples of the pulse wave signal are non-equidistantly spaced because the sampling rate is different in the first interval than as compared to the second interval. Put yet another way, samples corresponding to the first interval may be spaced more closely together than as compared to samples corresponding to the second interval.

The signal reconstructor 330 may generate an equidistantly sampled pulse wave signal by resampling the non-equidistant pulse wave signal measured by the pulse wave sensor 210. In this case, the signal reconstructor 330 may use various resampling methods.

The sampling profile manager 340 may identify an onset point of a heartbeat, a systolic period of a heartbeat, and a heartbeat cycle by analyzing the equidistant pulse wave signal generated by the signal reconstructor 330. In addition, the sampling profile manager 340 may update the sampling profile 360 based on the identified onset point of a heartbeat, a systolic period of a heartbeat, and a heartbeat cycle. For example, the sampling profile manager 340 may divide the equidistant pulse wave signal by cycle, identify a local minimum point of the equidistant pulse wave signal divided by cycle as an onset point of a heartbeat, and identify a cycle of the equidistant pulse wave signal as a heartbeat cycle. In addition, the sampling profile manager 340 may obtain a second-order derivative signal of the equidistant pulse wave signal divided by period, identify the third local maximum point of the second-order derivative signal, and identify that a period from the onset point of the heartbeat to the third local maximum point is a systolic period of the heartbeat.

The health index identifier 350 may identify a health index (e.g., heart rate, blood vessel stiffness, stress index, blood pressure, and the like) by analyzing the equidistant pulse wave signal generated by the signal reconstructor 330. For example, the health index identifier 350 may identify an onset point of a heart beat and a heartbeat cycle from the equidistant pulse wave signal, and identify a heart rate of the object of interest. In another example, the health index identifier 350 may identify blood vessel stiffness of the object of interest using a PAT scheme. In still another example, the health index identifier 350 may identify heart rate variability, and identify a stress index of the object of interest based on the heart rate variability. In yet another example, the health index estimator 350 may measure blood pressure of the object of interest using a PWA method.

According to an example embodiment, sampling rates are set differently in two separate intervals. Alternatively, sampling rates may be set differently in three or more separate intervals.

Figure 4:
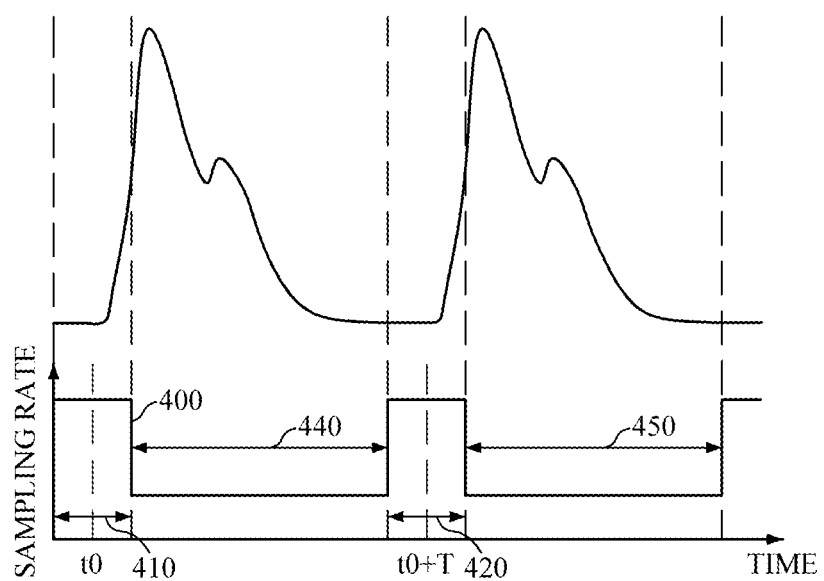
FIG. 4 is a diagram illustrating a sampling profile according to an example embodiment.

FIG. 4 is a diagram illustrating a sampling profile according to an example embodiment. The sampling profile in FIG. 4 may be used during identification of heart rate, stress index, or blood vessel stiffness.

Referring to FIG. 4, the sampling profile 400 for identifying heart rate, stress index, or blood vessel stiffness may store information that sets predetermined intervals 410 and 420 including onset points t0 and t0+T of heartbeats as first intervals to which a first sampling rate is to be applied, and sets the remaining intervals 440 and 450, other than the first intervals, as second intervals to which a second sampling rate that is less than the first sampling rate is to be applied. In the case of identification of heart rate, stress index, or blood vessel stiffness, the processor 300 may set a sampling rate of the pulse wave sensor 210 to the first sampling rate in the first intervals 410 and 420, and set the sampling rate of the pulse wave sensor 210 to the second sampling rate, that is less than the first sampling rate, in the second intervals 440 and 450. The processor 300 may set the sampling rates based on a sampling profile 400, and the pulse wave sensor 210 may sample a non-equidistant pulse wave signal based on the sampling rates set by the processor 300.

Figure 5:
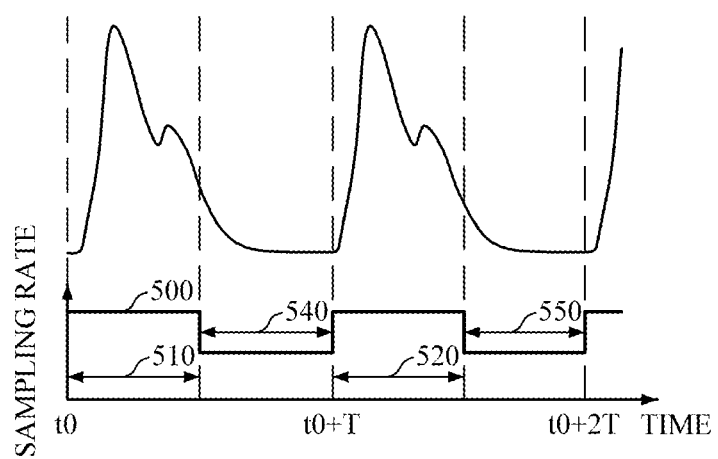
FIG. 5 is a diagram illustrating a sampling profile according to an example embodiment.

FIG. 5 is a diagram illustrating a sampling profile according to an example embodiment. The sampling profile shown in FIG. 5 may be used to identify blood pressure.

Referring to FIG. 5, a sampling profile 500 for identifying blood pressure may store information that identifies systolic periods 510 and 520 of heartbeats as first intervals to which a first sampling rate is to be applied, and that identifies the remaining intervals, i.e., diastolic periods 540 and 550, other than the first intervals, as second intervals to which a second sampling rate, which is less than the first sampling rate, is to be applied. In the case of identifying blood pressure, the processor 300 may set a sampling rate of the pulse wave sensor 210 to the first sampling rate in the first intervals 510 and 520, and set the sampling rate of the pulse wave sensor 210 to the second sampling rate, which is less than the first sampling rate, in the second intervals 540 and 550 based on the sampling profile 500. Further, the pulse wave sensor 210 may sample a non-equidistant pulse wave signal based on the sampling rates set by the processor 300.

Figure 6:
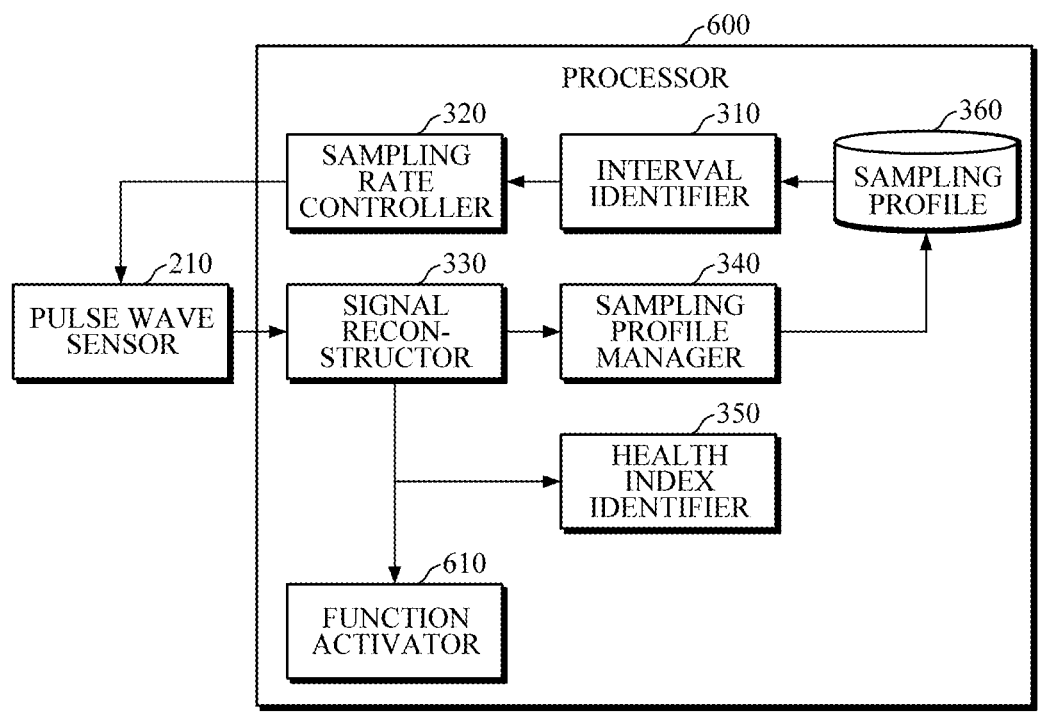
FIG. 6 is a block diagram illustrating a processor according to an example embodiment.

FIG. 6 is a block diagram illustrating a processor according to an example embodiment. A processor 600 shown in FIG. 6 may correspond to the processor 220 of FIG. 2.

Referring to FIG. 6, the processor 600 may include an interval identifier 310, a sampling rate controller 320, a signal reconstructor 330, a sampling profile manager 340, a health index identifier 350, and a function activator 610. Here, the interval identifier 310, the sampling rate controller 320, the signal reconstructor 330, the sampling profile manager 340, and the health index identifier 350 may be substantially the same as those described in association with FIG. 3, and hence detailed descriptions thereof are not reiterated.

The function activator 610 may activate or deactivate a sampling rate control function. The sampling rate control function may be a function of controlling a sampling rate of the pulse wave sensor 210 for each interval.

For example, the function activator 610 may deactivate the sampling rate control function based on the processor 600 identifying, as a result of analyzing an equidistant pulse wave signal, that the equidistant pulse wave signal is an abnormal heartbeat signal due to motion noise. When the sampling rate control function is deactivated, the sampling rate controller 320 may set a sampling rate of the pulse wave sensor 210 to a predetermined sampling rate, and the pulse wave sensor 210 may operate at the set sampling rate and measure an equidistantly sampled pulse wave signal. When the function activator 610 analyzes the equidistantly sampled pulse wave signal and identifies that the pulse wave signal is a normal heartbeat signal, the function activator 610 may re-activate the sampling rate control function.

Figure 7:
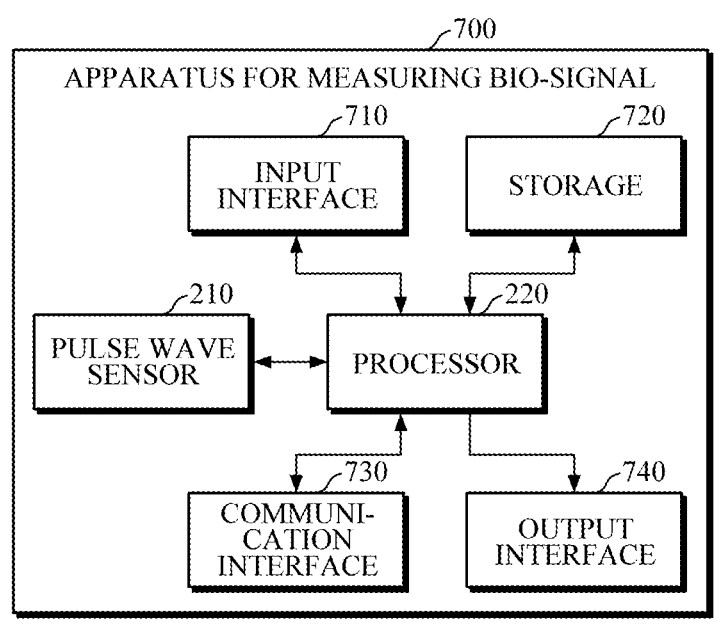
FIG. 7 is a block diagram illustrating an apparatus for measuring a bio-signal according to an example embodiment.

FIG. 7 is a block diagram illustrating an apparatus for measuring a bio-signal according to an example embodiment. The apparatus 700 for measuring a bio-signal shown in FIG. 7 may be disposed in the various electronic devices described elsewhere herein.

Referring to FIG. 7, the apparatus 700 for measuring a bio-signal may include a pulse wave sensor 210, a processor 220, an input interface 710, a storage 720, a communication interface 730, and an output interface 740. Here, the pulse wave sensor 210 and the processor 220 may be substantially the same as those described in association with FIG. 2, and therefore detailed descriptions thereof are not reiterated.

The input interface 710 may receive various operation signals based on a user input. According to an example embodiment, the input interface 710 may include a key pad, a dome switch, a touch pad (e.g., a resistive/capacitive touch pad), a jog wheel, a jog switch, a hardware button, and the like. In particular, when a touch pad has a layered structure with a display, the structure may be referred to as a touch screen.

Programs or commands for operation of the apparatus 700 for measuring a bio-signal may be stored in the storage 720, and data input to and output from the apparatus 700 for measuring a bio-signal may also be stored in the storage 720. In addition, a measured pulse wave signal, a sampling profile, an identified health index value, and the like, may be stored in the storage 720. The storage 720 may include at least one type of storage medium, such as a flash memory type, a hard disk type, a multimedia card micro type, a card type memory (e.g., SD or XD memory), random access memory (RAM), static random access memory (SRAM), read-only memory (ROM), electrically erasable programmable read-only memory (EEPROM), programmable read-only memory (PROM), a magnetic memory, a magnetic disk, and an optical disk. In addition, the apparatus 700 for measuring a bio-signal may communicate with an external storage medium, such as a web storage that performs the storage function of the storage 720 on the Internet.

The communication interface 730 may communicate with an external device. For example, the communication interface 730 may transmit the data input to, data stored in, and data processed in the apparatus 700 to the external device, and may receive various data that permits the apparatus 700 to generate/update the sampling profile and identify a health index from the external device.

In this case, the external device may be medical equipment that uses the data which is input to, stored in, or processed by the apparatus 700, or may be a printer or a display device that outputs results. In addition, the external device may include a digital TV, a desktop computer, a mobile phone, a smartphone, a tablet computer, a notebook computer, a PDA, a PMP, a navigation system, an MP3 player, a digital camera, a wearable device, and the like, but is not limited thereto.

The communication interface 730 may communicate with the external device using Bluetooth communication, Bluetooth low energy (BLE) communication, near field communication (NFC), wireless local access network (WLAN) communication, ZigBee communication, infrared data association (IrDA) communication, wireless fidelity (Wi-Fi) communication, ultra-wideband (UWB) communication, Ant+ communication, Wi-Fi direct (WFD) communication, radio frequency identification (RFID) communication, third generation (3G) communication, fourth generation (4G) communication, and fifth generation (5G) communication. However, these are merely examples and the types of communication are not limited thereto.

The output interface 740 may output the data input to, stored in, or processed by the apparatus 700 for measuring a bio-signal. According to an example embodiment, the output interface 740 may output the data input to, stored in, or processed by the apparatus 700 for measuring a bio-signal using at least one of an audible method, a visual method, and a tactile method. To this end, the output interface 740 may include a display, a speaker, a vibrator, and the like.

Figure 8:
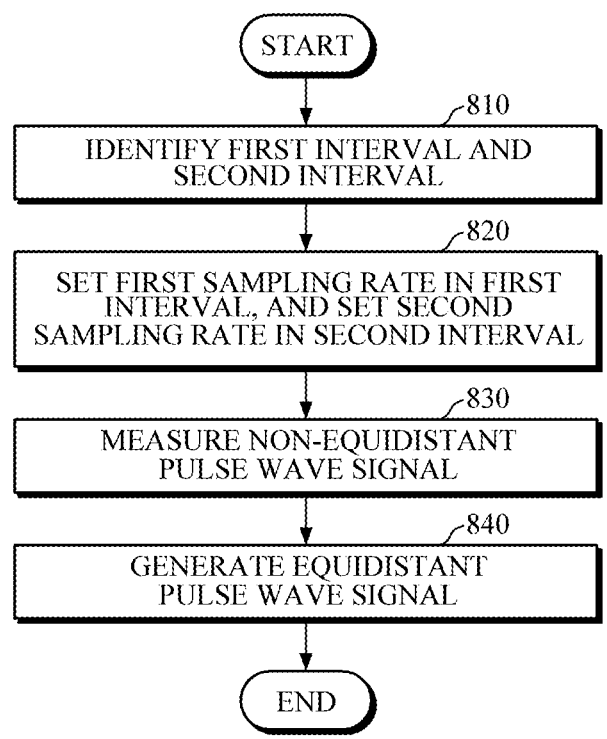
FIG. 8 is a flowchart illustrating a method of measuring a bio-signal according to an example embodiment.

FIG. 8 is a flowchart illustrating a method of measuring a bio-signal according to an example embodiment. The method shown in FIG. 8 may be performed by the apparatus 200 or the apparatus 700 for measuring a bio-signal of FIG. 2 or FIG. 7, respectively.

Referring to FIG. 8, the apparatus for measuring a bio-signal may identify a first interval to which a first sampling rate is to be applied, and a second interval to which a second sampling rate is to be applied (step 810). Further, the apparatus may identify the first interval and the second interval based on a health index to be measured. Further still, the apparatus may identify the first interval and the second interval using a sampling profile. In this case, the sampling profile may store information that maps a health index and first and second intervals corresponding to the health index, and may be generated in advance by analyzing a pulse wave signal of the object of interest. For example, when the health index is heart rate, stress index, or blood vessel stiffness, the sampling profile may store information that sets a predetermined interval including the onset point of the heartbeat as the first interval, and sets the remaining interval other than the first interval as the second interval. In addition, when the health index is blood pressure, the sampling profile may store information that sets a systolic period of the heartbeat as the first interval, and sets the remaining interval, i.e., a diastolic period of the heartbeat, other than the first interval as the second interval.

The apparatus for measuring a bio-signal may set a sampling rate of a pulse wave sensor to a first sampling rate in the first interval, and set the sampling rate of the pulse wave sensor to a second sampling rate in the second interval (step 820), and may measure a non-equidistant pulse wave signal based on the set sampling rate (step 830).

The apparatus for measuring a bio-signal may generate an equidistant pulse wave signal by resampling the measured non-equidistant pulse wave signal (step 840). In this case, the apparatus for measuring a bio-signal may use various resampling methods.

Figure 9:
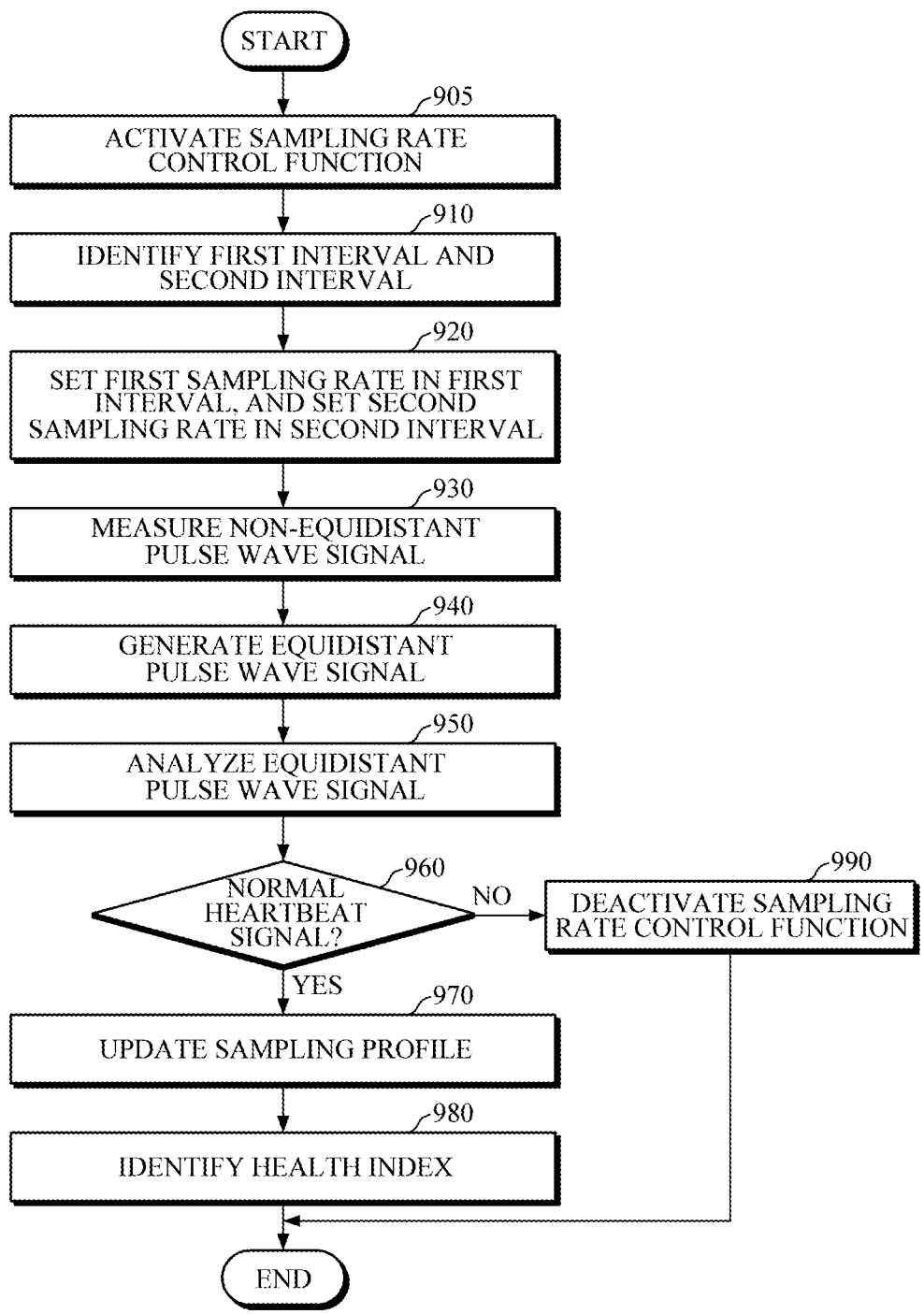
FIG. 9 is a flowchart illustrating a method of measuring a bio-signal according to an example embodiment.

FIG. 9 is a flowchart illustrating a method of measuring a bio-signal according to an example embodiment. The method shown in FIG. 9 may be performed by the apparatus 200 or the apparatus 700 for measuring a bio-signal shown in FIG. 2 or FIG. 7, respectively.

Referring to FIG. 9, the apparatus for measuring a bio-signal may activate a sampling rate control function (step 905), and may identify a first interval to which a first sampling rate is to be applied, and a second interval to which a second sampling rate is to be applied based on a health index to be identified (step 910). The sampling rate control function may be a function of controlling a sampling rate of the pulse wave sensor for each interval.

The apparatus for measuring a bio-signal may set a sampling rate of the pulse wave sensor to the first sampling rate in the first interval, and set the sampling rate of the pulse wave sensor to the second sampling rate in the second interval (step 920), and may measure a non-equidistant pulse wave signal (step 930).

The apparatus for measuring a bio-signal may generate an equidistant pulse wave signal by resampling the measured non-equidistant pulse wave signal (step 940).

The apparatus for measuring a bio-signal may identify an onset point of a heartbeat, a systolic period of a heartbeat, and a heartbeat cycle by analyzing the equidistant pulse wave signal (step 950). For example, the apparatus for measuring a bio-signal may divide the equidistant pulse wave signal by cycle, identify a local minimum point of the equidistant pulse wave signal divided by cycle as an onset point of a heartbeat, and identify a cycle of the equidistant pulse wave signal as a heartbeat cycle. In addition, the apparatus for measuring a bio-signal may obtain a second-order derivative signal of the equidistant pulse wave signal divided by a period, identify the third local maximum point of the second-order derivative signal, and identify that a period from the onset point of the heartbeat to the third local maximum point is a systolic period of the heartbeat.

If the apparatus for measuring a bio-signal identifies, as a result of analyzing the equidistant pulse wave signal, that the equidistant pulse wave signal is an abnormal heartbeat signal (step 960—NO), then the apparatus for measuring a bio-signal may deactivate the sampling rate control function (step 990).

If the apparatus for measuring a bio-signal identifies, as a result of analyzing the equidistant pulse wave signal, that the equidistant pulse wave signal is a normal heartbeat signal (step 960—YES), then the apparatus for measuring a bio-signal may update the sampling profile based on the onset point of a heartbeat, the systolic period of a heartbeat, and the heartbeat cycle, which are identified in step 950 (step 970).

The apparatus for measuring a bio-signal may identify a health index (e.g., heart rate, blood vessel stiffness, stress index, blood pressure, etc.) based on the equidistant pulse wave signal (step 980). For example, the apparatus for measuring a bio-signal may identify a heart rate of an object of interest based on the onset point of a heartbeat and the heartbeat cycle identified from the equidistant pulse wave signal. In another example, the apparatus for measuring a bio-signal may identify blood vessel stiffness of the object of interest using a PAT scheme. In still another example, the apparatus for measuring a bio-signal may identify blood pressure of the object of interest using a pulse waveform analysis (PWA) scheme.

Meanwhile, when a sampling rate control function is deactivated (e.g., in step 990), the apparatus for measuring a bio-signal may set a pulse wave sensor to a predetermined sampling rate, and measure an equidistantly sampled pulse wave signal. In addition, the apparatus for measuring a bio-signal may analyze the equidistantly sampled pulse wave signal, and may re-activate the sampling rate control function based on identifying that the pulse wave signal is a normal heartbeat signal.

Figure 10:
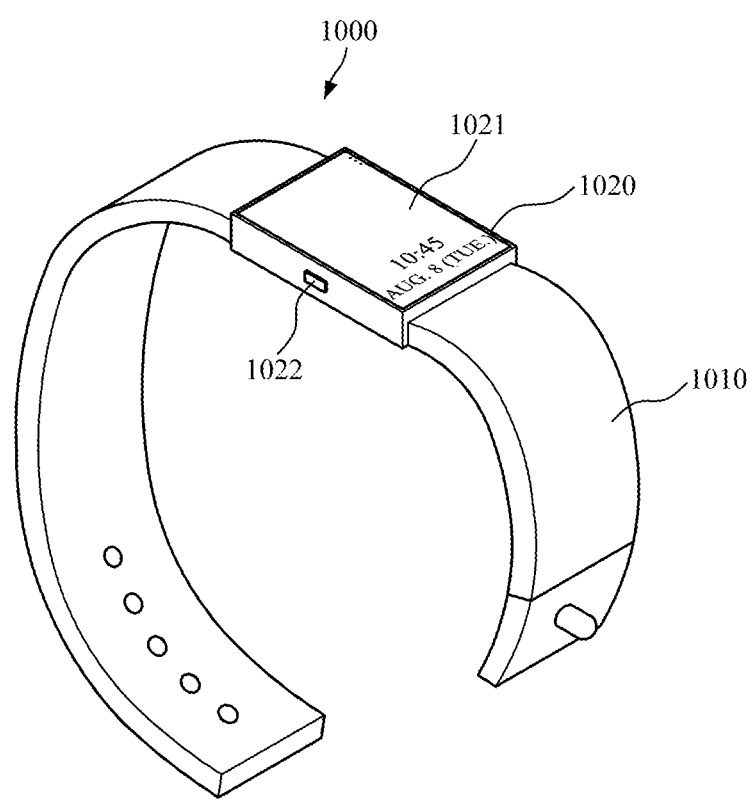
FIG. 10 is a diagram illustrating a wrist-type wearable device according to an example embodiment.

FIG. 10 is a diagram illustrating a wrist-type wearable device according to an example embodiment.

Referring to FIG. 10, the wrist-type wearable device 1000 may include a strap 1010, and a main body 1020.

The strap 1010 may be divided into two members that are connected to each end of the main body 1020, and that are capable of being coupled to each other. Alternatively, the strap 1010 may be integrally formed in the form of a smart band. The strap 1010 may be formed of a flexible material that wraps around a user's wrist such that the main body 1020 can be placed on the user's wrist.

The main body 1020 may include the above-described apparatus 200 or apparatus 700 for measuring a bio-signal disposed therein. In addition, a battery for supplying power to the wrist-type wearable device 1000 and the apparatus 200 or apparatus 700 for measuring a bio-signal may be embedded in the main body 1020.

A pulse wave sensor may be disposed in a lower part of the main body 1020 such that the pulse wave sensor is exposed to the wrist of the user. Accordingly, when the user wears the wrist-type wearable device 1000, the pulse wave sensor may be naturally brought into contact with the skin of the user. In this case, the pulse wave sensor may emit light towards the skin of the user, and acquire a pulse wave signal of the user by receiving light reflected by or scattered from the skin.

The wrist-type wearable device 1000 may further include a display 1021 and an input interface 1022, which are disposed on the main body 1020. The display 1021 may display data processed by the wrist-type wearable device 1000 and the apparatus 200 or apparatus 700 for measuring a bio-signal and processing result data. The input interface 1022 may receive various operation signals based on a user input.

The example embodiments may be implemented as computer readable code stored in a non-transitory computer-readable medium. Code and code segments constituting the computer program may be inferred by a person skilled in the art. The computer-readable medium includes all types of recording media in which computer-readable data is stored. Examples of the computer-readable medium may include a ROM, a RAM, a CD-ROM, a magnetic tape, a floppy disk, and an optical data storage. Further, the computer-readable medium may be implemented in the form of a carrier wave such as Internet transmission. In addition, the computer-readable medium may be distributed to computer systems over a network, in which computer-readable code may be stored and executed in a distributed manner.

A number of examples have been described above. Nonetheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for measuring a bio-signal, the apparatus comprising:
   a pulse wave sensor configured to measure a pulse wave signal of a single heartbeat, of an object of interest, that is non-equidistantly sampled based on a sampling rate of the pulse wave sensor; and
   a processor configured to:
   identify, using a sampling profile, a first interval of the single heartbeat based on a health index to be measured, among a plurality of health indexes comprising at least one of a heart rate, a blood vessel stiffness, a stress index, and a blood pressure;
   identify, using the sampling profile, a second interval of the single heartbeat based on the health index to be measured;
   set the sampling rate of the pulse wave sensor to a first sampling rate in the first interval of the single heartbeat; and
   set the sampling rate of the pulse wave sensor to a second sampling rate in the second interval of the single heartbeat, the second sampling rate being less than the first sampling rate,
   wherein the sampling profile comprises the first interval that corresponds to each of the plurality of health indexes.

2. The apparatus of claim 1, wherein the pulse wave signal is a photoplethysmogram signal.

3. The apparatus of claim 1, wherein the plurality of health indexes comprises a first health index and a second health index,
   the first health index corresponds to the heart rate, the blood vessel stiffness, or the stress index,
   the second health index corresponds to the blood pressure, and
   the sampling profile indicates that the first interval corresponding to the first health index is different from the first interval corresponding to the second health index.

4. The apparatus of claim 1, wherein the processor is further configured to:
   identify a predetermined interval including an onset point of the single heartbeat as the first interval of the single heartbeat; and identify a remaining interval of the single heartbeat as the second interval of the single heartbeat, based on the health index to be measured being at least one of the heart rate, the blood vessel stiffness, and the stress index.

5. An apparatus for measuring a bio-signal, the apparatus comprising:
a pulse wave sensor configured to measure a pulse wave signal of a single heartbeat, of an object of interest, that is non-equidistantly sampled based on a sampling rate of the pulse wave sensor; and
a processor configured to:
identify, using a sampling profile, a systolic period of the single heartbeat as a first interval of the single heartbeat, based on a health index to be measured;
identify, using the sampling profile, a remaining interval of the single heartbeat as a second interval of the single heartbeat, based on the health index to be measured;
set the sampling rate of the pulse wave sensor to a first sampling rate in the first interval of the single heartbeat; and
set the sampling rate of the pulse wave sensor to a second sampling rate in the second interval of the single heartbeat, the second sampling rate being less than the first sampling rate.

6. The apparatus of claim 1, wherein the processor is further configured to generate an equidistantly sampled pulse wave signal by resampling the non-equidistantly sampled pulse wave signal.

7. The apparatus of claim 6, wherein the processor is further configured to:
identify at least one of an onset point of the single heartbeat, a systolic period of the single heartbeat, and a heartbeat cycle by analyzing the generated equidistantly sampled pulse wave signal; and
update the sampling profile based on the onset point of the single heartbeat, the systolic period of the heartbeat, or the heartbeat cycle.

8. The apparatus of claim 6, wherein the processor is further configured to identify the health index by analyzing the equidistantly sampled pulse wave signal.

9. The apparatus of claim 6, wherein the processor is further configured to:
identify that the equidistantly sampled pulse wave signal is an abnormal heartbeat signal; and
deactivate a sampling rate control function based on identifying that the equidistantly sampled pulse wave signal is the abnormal heartbeat signal.

10. A method of measuring a bio-signal, the method comprising:
identifying, using a sampling profile, a first interval of a single heartbeat and a second interval of the single heartbeat based on a health index to be measured, among a plurality of health indexes comprising at least one of a heart rate, a blood vessel stiffness, a stress index, and a blood pressure;
setting a sampling rate of a pulse wave sensor to a first sampling rate in the first interval of the single heartbeat;
setting the sampling rate of the pulse wave sensor to a second sampling rate in the second interval of the single heartbeat, the second sampling rate being less than the first sampling rate; and
measuring a pulse wave signal of an object of interest that is non-equidistantly sampled based on the sampling rate of the pulse wave sensor,
wherein the sampling profile comprises the first interval that corresponds to each of the plurality of health indexes.

11. The method of claim 10, wherein the pulse wave signal is a photoplethysmogram signal.

12. The method of claim 10, wherein the plurality of health indexes comprises a first health index and a second health index,
the first health index corresponds to the heart rate, the blood vessel stiffness, or the stress index,
the second health index corresponds to the blood pressure, and
the sampling profile indicates that the first interval corresponding to the first health index is different from the first interval corresponding to the second health index.

13. The method of claim 10, wherein the identifying of the first interval of the single heartbeat and the second interval of the single heartbeat comprises identifying a predetermined interval including an onset point of the single heartbeat as the first interval of the single heartbeat and identifying a remaining interval of the single heartbeat as the second interval of the single heartbeat based on the health index to be measured being the heart rate, the blood vessel stiffness, or the stress index.

14. A method of measuring a bio-signal, the method comprising:
identifying a systolic period of a single heartbeat as a first interval of the single heartbeat and identifying a remaining interval of the single heartbeat as a second interval of the single heartbeat, based on a sampling profile and a health index to be measured;
setting a sampling rate of a pulse wave sensor to a first sampling rate in the first interval of the single heartbeat;
setting the sampling rate of the pulse wave sensor to a second sampling rate in the second interval of the single heartbeat, the second sampling rate being less than the first sampling rate; and
measuring a pulse wave signal of an object of interest that is non-equidistantly sampled based the sampling rate of the pulse wave sensor.

15. The method of claim 10, further comprising generating an equidistantly sampled pulse wave signal by resampling the non-equidistantly sampled pulse wave signal.

16. The method of claim 15, further comprising:
identifying at least one of an onset point of the single heartbeat, a systolic period of the single heartbeat, and a heartbeat cycle by analyzing the generated equidistantly sampled pulse wave signal; and
updating the sampling profile based on least one of the onset point of the heartbeat, the systolic period of the heartbeat, or the heartbeat cycle.

17. The method of claim 15, further comprising identifying the health index by analyzing the equidistantly sampled pulse wave signal.

18. The method of claim 15, further comprising:
identifying that the equidistantly sampled pulse wave signal is an abnormal heartbeat signal; and
deactivating a sampling rate control function based on identifying that the equidistantly sampled pulse wave signal is the abnormal heartbeat signal.

19. A wearable device for measuring a heartbeat of a user, comprising:
a photoplethysmogram (PPG) sensor configured to emit light towards a skin surface of the user of the wearable device based on a sampling rate of the PPG sensor; and
a processor configured to:
set the sampling rate of the PPG sensor to a first sampling rate during a systolic portion of the heartbeat of the user; and set the sampling rate of the PPG sensor to a second sampling rate, that is less than the first sampling rate, during a diastolic portion of the heartbeat of the user.

\* \* \* \* \*